United States Patent [19]

Heiss

[11] 4,031,136
[45] June 21, 1977

[54] PROCESS FOR THE PREPARATION OF TRANS, TRANS-MUCONIC ACID

[75] Inventor: Lorenz Heiss, Hofheim, Taunus, Germany

[73] Assignee: Hoechst Aktiengesellschaft, Frankfurt am Main, Germany

[22] Filed: Jan. 22, 1976

[21] Appl. No.: 651,263

[30] Foreign Application Priority Data

Jan. 28, 1975 Germany .......................... 2503313

[52] U.S. Cl. .................... 260/537 N; 260/475 FR; 260/484 P
[51] Int. Cl.$^2$ ........................................ C07C 51/09
[58] Field of Search .................. 260/537 N, 484 P

[56] References Cited

UNITED STATES PATENTS

| 2,534,212 | 12/1950 | Wacek | 260/537 N |
| 3,429,949 | 2/1969 | Driscoll | 260/537 N |

FOREIGN PATENTS OR APPLICATIONS

| 43,489 | 1/1968 | Japan | 260/537 N |

*Primary Examiner*—Vivian Garner
*Attorney, Agent, or Firm*—Connolly and Hutz

[57] ABSTRACT

Process for the preparation of trans, trans-muconic acid by reacting a glyoxalacetal with ketene in the presence of an acid catalyst and hydrolyzing the $\beta,\beta'$-dialkoxy-adipic acid-alkylester formed with alkali. By this new process trans, trans-muconic acid is easily obtained in better yield, which compound is an important intermediate for the production of 1,4-naphthalene-dicarboxylic acid esters.

2 Claims, No Drawings

PROCESS FOR THE PREPARATION OF TRANS, TRANS-MUCONIC ACID

The present invention relates to a process for the preparation of trans, trans-muconic acid.

It has been known how to prepare trans, trans-muconic acid by way of bromination and dehydrobromination of adipic acid (Annalen 256, 1; Ingold, J. Chem. Soc. 119 (1921) 951; Farmer, J. Chem. Soc. 123 (1923) 2531 as well as Org. Synth. Vol. III, 623). However, this synthesis is rather time-consuming, and the yields are moderate, so that its use on a technical scale is hardly to be considered.

It has now been found that trans, trans-muconic acid can be obtained in a high yield, if glyoxalacetals are reacted with ketene in the presence of acid catalysts, at a temperature of from −30° to +60° C, optionally in a solvent, and the $\beta,\beta'$-dialkoxy-adipic acid-alkyl-ester formed is hydrolyzed with alkali.

As glyoxalacetals there may be mentioned those acetals which are derived from alcohols having from 1 to 4, preferably 1 to 2 carbon atoms. They are prepared according to known methods, for example, in the case of the glyoxalmethylacetal, by boiling glyoxal (of 80 % strength) for several hours in excess methanol, in the presence of acids as catalysts. After the methanol has been removed, the glyoxal-methylacetal (tetramethoxyethane) may be obtained in its pure form by distillation.

The reaction of the glyoxalacetals with ketene is effected in the presence of Lewis acids, such as $ZnCl_2$, $AlCl_3$ or preferably in the presence of $BF_3$-etherate, at a temperature in the range of from −30° to 60° C. The reaction may also be carried out in the presence of an inert solvent, such as diethylether, benzene or toluene. It follows the scheme indicated below:

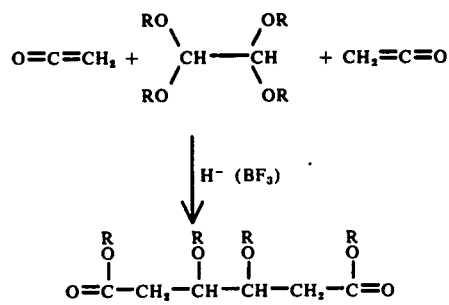

The $\beta, \beta'$-dialkoxy-adipic acid-alkylester thus formed is then split to yield trans, trans-muconic acid by a treatment with alkali, such as aqueous sodium hydroxide solution, and the acid may be isolated in usual manner by acidifying and filtering from the reaction mixture.

Muconic acid and the derivatives thereof represent interesting compounds which may be polymerized to yield valuable products. Their esters may be reacted as dienes with Δ1-pyrrolidino-cyclohexene to give hexahydronaphthalene-1,4-dicarboxylic acid-ester which, after dehydration, yields 1,4-naphthalene-dicarboxylic acid-ester. This latter substance is an important intermediate product for the preparation of optical brighteners.

The following Example serves to illustrate the invention.

EXAMPLE

At a temperature of 0° C, about 65 ml of ketene were introduced — in the course of about 2 to 3 hours — into 90 g (0.6 mole) of tetramethoxymethane (glyoxalmethylacetal), to which 16 ml of $BF_3$-etherate had been added, together with dry nitrogen, the mixture being well stirred and cooled. The stirring was continued for 1 hour at room temperature, then the reaction mixture was diluted with ether, and the ether phase was shaken out twice each time with aqueous sodium chloride solution, in which 30 g of $KHCO_3$ had been dissolved, and then with pure sodium hydroxide solution. The ether phase was dried with sodium sulfate, was filtered, the ether was eliminated and the raw reaction product was distilled at 0.4 Torr. Boiling point: 108° to 109° C. Refractive index $n_{20}{}^D = 1.4368$. Yield: 121 Grams (86.5 % of the theory) of $\beta, \beta'$-dimethoxy-adipic acid-dimethylester.

23.5 Grams (0.1 mole) of $\beta, \beta'$-dimethoxy-adipic acid-dimethylester were boiled under reflux with a solution of 32 g of NaOH in 50 ml of water for 8 hours, were cooled, suction-filtered, dissolved in water, were precipitated with concentrated hydrochloric acid at a pH value of 1, were washed with water until neutral and dried. 12.2 Grams (86 % of the theoretical yield) of trans, trans-muconic acid were obtained which had a melting point of from 298° to 300° C.

I claim:

1. Process for the preparation of trans, trans-muconic acid, which comprises reacting a glyoxalacetal with ketene at a temperature of from minus 30° to plus 60° C in the presence of a Lewis acid catalyst and hydrolyzing the $\beta, \beta'$-dialkoxy-adipic acid-alkylester formed with alkali.

2. Process as claimed in claim 1, which comprises carrying out the reaction in the presence of an inert solvent.